(12) United States Patent
Tsukashima et al.

(10) Patent No.: US 7,736,320 B2
(45) Date of Patent: Jun. 15, 2010

(54) SELF-CONDENSING PH SENSOR AND CATHETER APPARATUS

(75) Inventors: Ross Tsukashima, San Diego, CA (US); Erich H. Wolf, Vista, CA (US); Jeffery D. Schipper, Ramona, CA (US); Charles S. Bankert, Oceanside, CA (US); Leo R. Roucher, Rancho Santa Fe, CA (US); Thomas Germain Wallner, San Marcos, CA (US)

(73) Assignee: Sierra Medical Technology, Inc., San Diego, CA (US)

( * ) Notice: Subject to any disclaimer, the term of this patent is extended or adjusted under 35 U.S.C. 154(b) by 1403 days.

(21) Appl. No.: 11/137,600

(22) Filed: May 25, 2005

(65) Prior Publication Data

US 2006/0270940 A1 Nov. 30, 2006

(51) Int. Cl.
*A61B 5/08* (2006.01)
(52) U.S. Cl. .................. 600/529; 600/361; 600/547; 204/433; 436/68; 324/438
(58) Field of Classification Search .............. 600/361, 600/306, 300, 301, 547; 204/433; 436/68; 324/438
See application file for complete search history.

(56) References Cited

U.S. PATENT DOCUMENTS

| 4,567,882 | A | * | 2/1986 | Heller ..................... 600/249 |
| 4,981,470 | A | * | 1/1991 | Bombeck, IV .............. 600/350 |
| 5,411,022 | A | * | 5/1995 | McCue et al. ............... 600/361 |
| 5,477,860 | A | * | 12/1995 | Essen-Moller .............. 600/529 |
| 5,690,642 | A | * | 11/1997 | Osborne et al. ............. 623/1.11 |
| 5,692,497 | A | * | 12/1997 | Schnitzer et al. ....... 128/204.21 |
| 5,891,030 | A | * | 4/1999 | Johnson et al. ............. 600/407 |
| 2002/0042565 | A1 | * | 4/2002 | Cooper et al. ................ 600/407 |
| 2004/0171962 | A1 | * | 9/2004 | Leveque et al. ............. 600/547 |
| 2005/0181010 | A1 | * | 8/2005 | Hunter et al. ............... 424/423 |
| 2006/0167531 | A1 | * | 7/2006 | Gertner et al. ................ 607/86 |

\* cited by examiner

*Primary Examiner*—Robert L Nasser
*Assistant Examiner*—Michael D'Angelo
(74) *Attorney, Agent, or Firm*—Michael Klicpera

(57) ABSTRACT

The present invention is a system for monitoring a patient's breath chemistry comprising a plurality of components, including a self-condensing pH sensor distally mounted on a catheter, a transmitter with hydration sensing circuitry for the pH sensor, and, a processing receiver/data recorder. The specifically designed self-condensing pH sensor located on the distal end of the catheter is designed to be inserted into the patient's airway. Monitoring of a patient's breath pH is accomplished by using the miniaturized self-condensing pH sensor, providing for real-time monitoring of patient airway pH values.

47 Claims, 5 Drawing Sheets

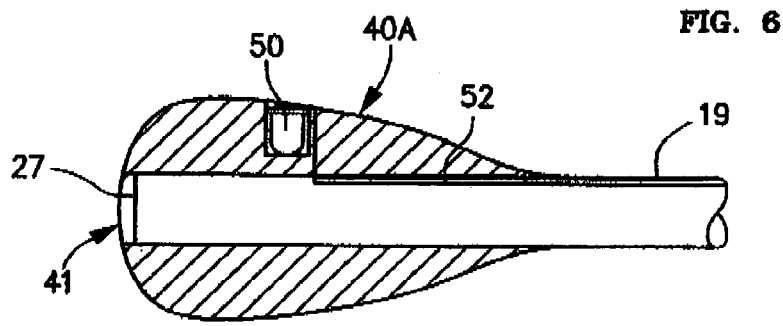
FIG. 6
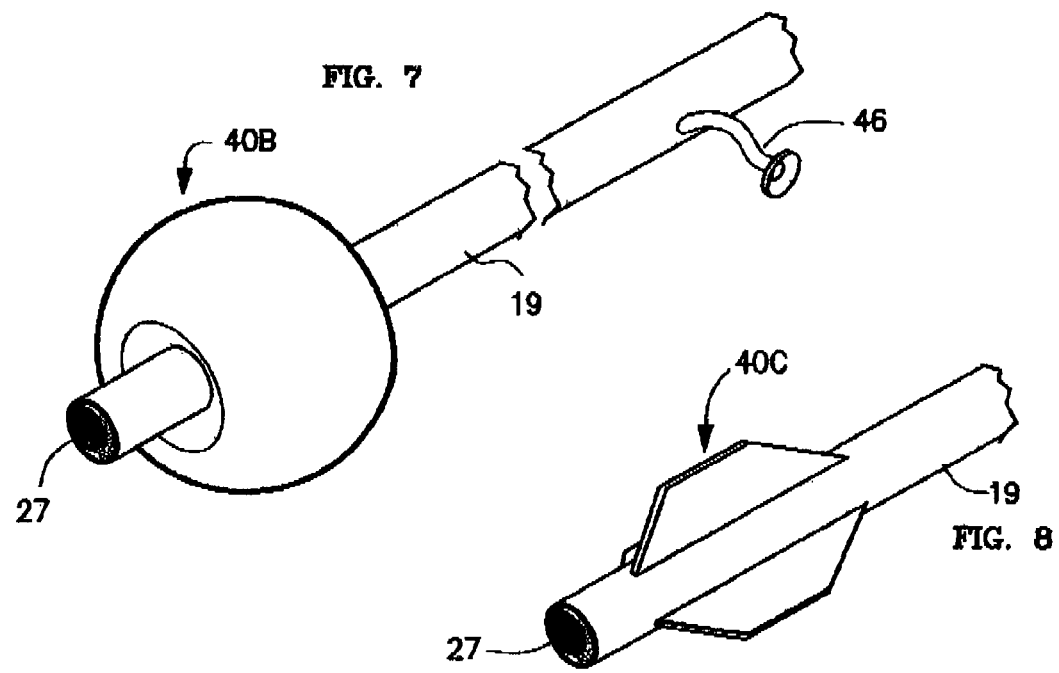
FIG. 7
FIG. 8
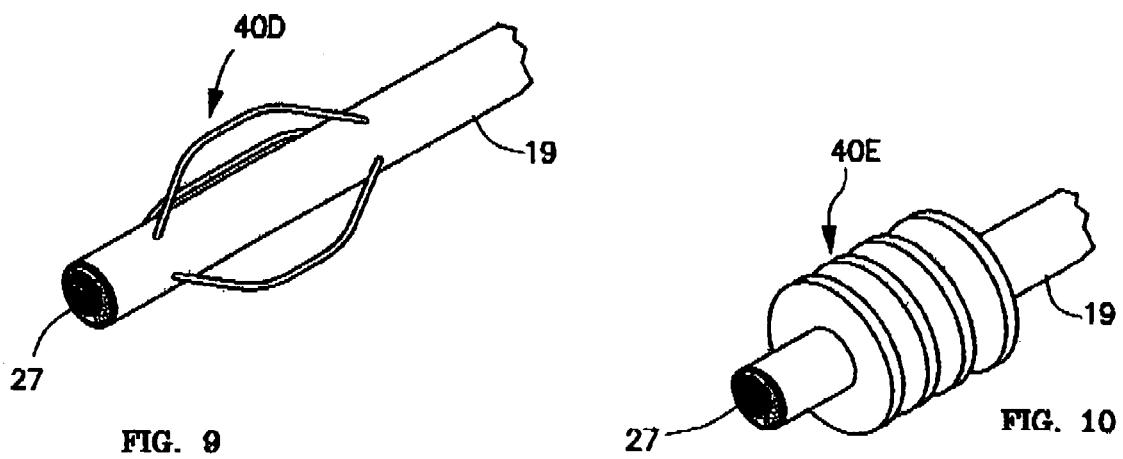
FIG. 9
FIG. 10

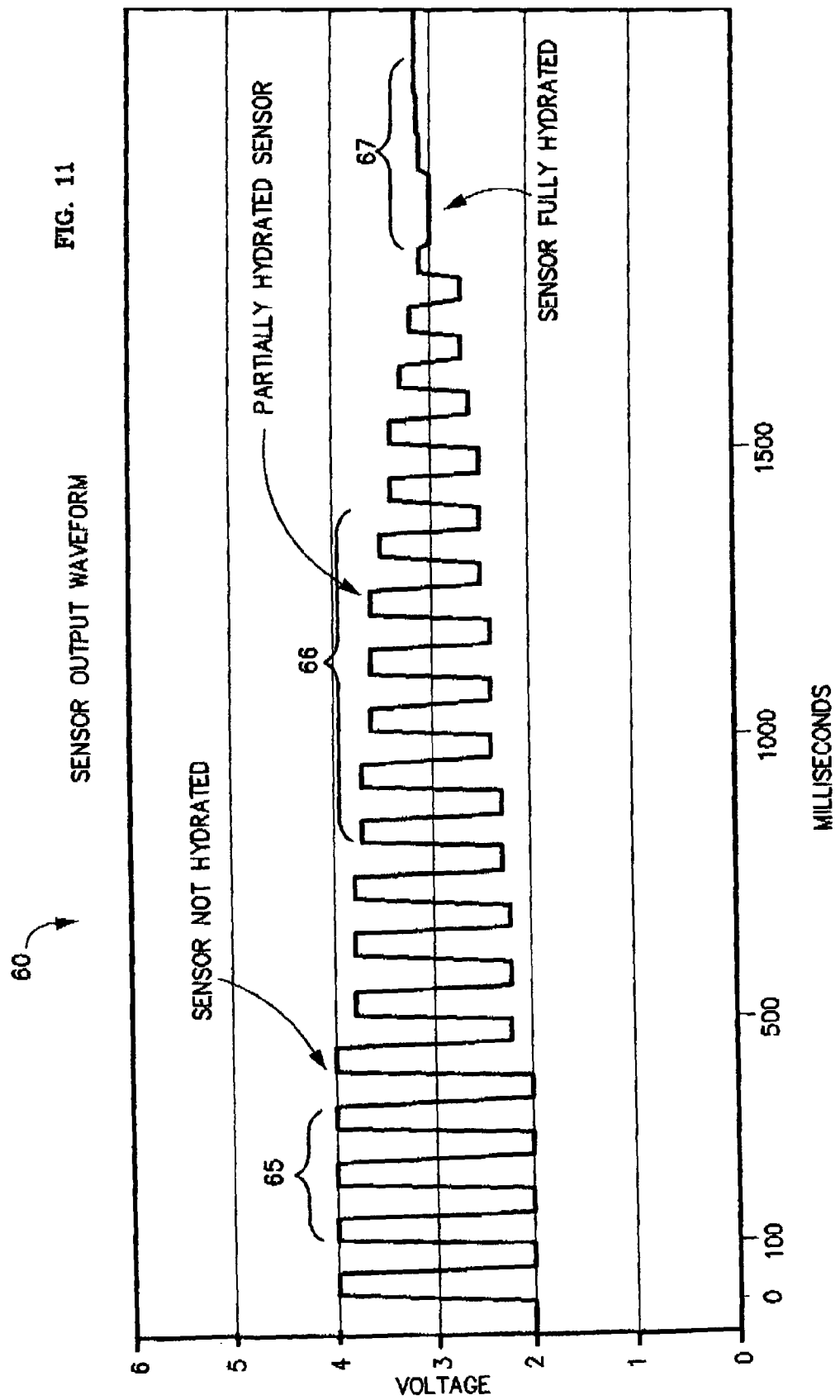

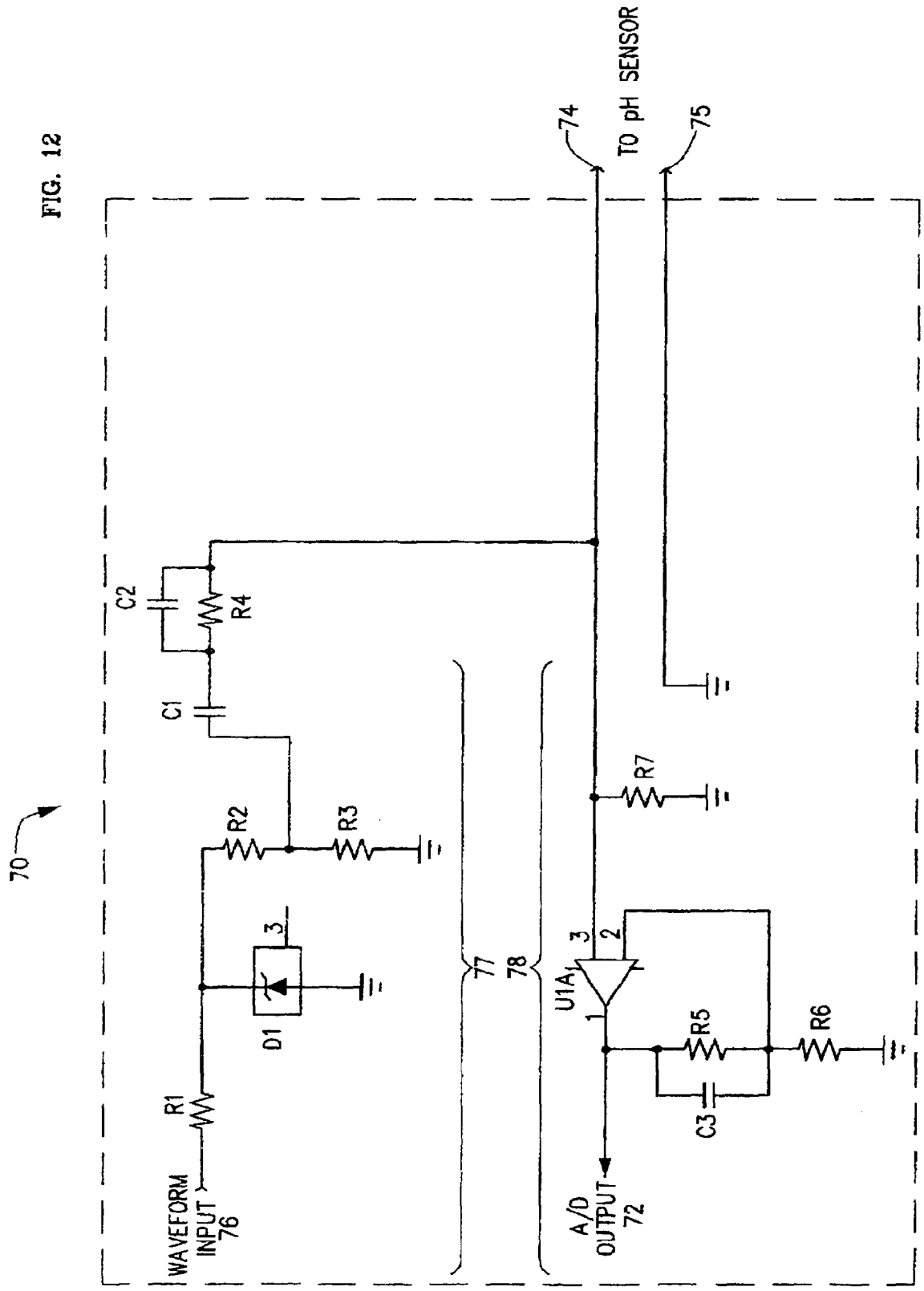

SELF-CONDENSING PH SENSOR AND CATHETER APPARATUS

FIELD OF THE INVENTION

The field of art to which this invention relates is in the monitoring of breath chemistry in a patient's airway to provide information that enables physicians to diagnose certain respiratory diseases associated with gastroesophageal reflux (GER). More specifically, the present invention measures the pH level of a patient's breath and provides for real time monitoring.

BACKGROUND OF THE INVENTION

Recently, it has been reported that the monitoring of acidity or pH of a patient's breath could help physicians in estimating the potential for and occurrence of asthma, laryngopharyngeal reflux disease (LPRD), aspiration-related lung diseases, chronic obstructive pulmonary disease (COPD), and sleep related breathing disorders such as obstructive sleep apnea (OSA).

Gastroesophageal reflux in the airway is associated with, and known to exacerbate, widespread respiratory diseases such as asthma, laryngopharyngeal reflux disease (LPRD), aspiration-related lung diseases, chronic obstructive pulmonary disease (COPD), and sleep related breathing disorders such as obstructive sleep apnea (OSA). Reflux in the airway is also prevalent in infants and children as well as intubated or sedated patients in whom current pH diagnostic procedures are contraindicated. In extreme cases, the exposure of acid reflux into the respiratory system can lead to aspiration pneumonia or acute respiratory distress.

Given the current state of commercialized products, clinicians are limited in their ability to test pH in the respiratory tract. Evaluation of patient pH can be conducted by a qualified physician in a typical 24 hour pH study, using a pH measurement catheter. The presently available pH monitoring and diagnostic devices require insertion of a pH measurement catheter through a patient's nose, past the epiglottis, through the upper esophageal sphincter (UES), and into the esophagus. These catheters are comprised of a pH sensor and reference sensor at the catheter distal end, and require immersion in liquid to function effectively. The devices have invasive or uncomfortable consequences for the patient. Because they pass through the larynx and into the esophagus, discomfort during swallowing, talking, and movement can occur. A recently introduced product, the Medtronic Bravo™, is a catheter based device that requires attachment of a pH measurement capsule to the esophagus wall. The product requires a larger diameter trans-nasal catheter to place the capsule. Because these methods are invasive and uncomfortable, only a small percentage of prospective patients are able to undergo pH monitoring.

Placement of esophageal catheters requires special expertise to identify the physical landmarks required for proper catheter placement. Typically, pressure measurements are conducted to find the lower esophageal sphincter and upper esophageal sphincter, with endoscopic confirmation of placement required in some cases.

Traditional pH catheters used to conduct measurements of pH in the patient's laryngeal region and have several limitations when placed in the upper airway. They are capable of only measuring liquid reflux events which extend past the UES. They are subject to becoming fouled, contaminated or embedded in the mucosal wall. If placed higher in the airway, the sensor can become dehydrated, losing electrical continuity with the reference electrode. In these cases, the accuracy and reliability of the pH, measurements are compromised.

Accordingly, there is a need for a novel pH monitoring system with electronic or wireless communication linked to a processing receiver with data recording capability that can reliably measure and record pH in the patient's airway in real time.

SUMMARY OF THE INVENTION

The present invention pertains to a device for monitoring the breath chemistry of a patient's exhaled breath in real-time. The present invention is a system comprising a self-condensing pH sensor distally mounted on a catheter, a transmitter with hydration sensing circuitry for the pH sensor, and processing receiver/data recorder. The self-condensing pH sensor located on the distal end of a tubular catheter is designed to be inserted into the patient's upper airway, and more specifically, into the oropharynx region of a patient's upper airway. Due to the design, position on the distal end of the catheter, the size of the pH sensor, and location in the patient's airway, the pH sensor of the present invention is self condensing. In the humid gaseous environment of the oropharynx region, fluid condenses and deposits on the terminal surface of the pH sensor and creates an ion path between the reference wick and the antimony element. The catheter has at least one lumen that extends along the longitudinal length of the catheter. The self-condensing pH sensor uses the catheter shaft as its outer tubular member to house a silver chloride reference element, an ion conducting path, and an antimony sensor element isolated in an inner tubular member that is co-linearly or coaxially configured within the catheter tubular member. The performance of the self-condensing sensor may be enhanced by including a hygroscopic coating. A separation means may be employed in close proximity to the pH sensor to keep the pH sensor from directly contacting the mucosal tissue of the patient's oropharynx region, to prevent the pH sensor from becoming entrapped in the airway mucosal wall which could impair the sensor's ability to measure the airway pH. Centimeter markings are imprinted on the catheter shaft to aid in proper positioning and placement. An optional lighting source is also located in the distal end of the catheter to simplify placement of the self-condensing sensor in the oropharynx region. The optional lighting of the present invention addresses catheter insertion and location with a innovative method of placement, using a continuous or flashing light emitting diode (LED) embedded in the distal end of the catheter to provide a visual sighting means for the physician.

A transmitter with an antenna is located at the proximal end of the catheter and transfers the observed pH data by employing one of many wireless methods, such as radio-frequency (RF) energy. Alternately, the transfer of observed pH data is accomplished by direct wire methods. The transmitter also includes a means to evaluate the signal strength from the pH sensor to determine whether the sensor is hydrated sufficiently to accurately measure pH. This is accomplished by periodically sending a low voltage signal to the pH sensor and analyzing the resulting wave forms.

The pH data is transferred or updated at specific intervals, which can be varied according to the patient's needs, to a processing receiver that has the capability to record the pH data over time. The processing receiver/data recorder includes a removable data card that stores the recorded pH data for subsequent analysis. The processing receiver/data recorder can also include a visual or audible alarming means that is generated upon when predetermined pH values are detected.

In operation, the distally mounted pH sensor/catheter assembly is inserted through one of the patient's nostrils until the self-condensing pH sensor is positioned in the oropharynx region, typically above the epiglottis. When the pH sensor is located in the proper position, a securing means is used to fasten the pH sensor/catheter assembly in place.

These and other features, aspects and advantages of the present invention will become better understood with reference to the following descriptions and claims.

BRIEF DESCRIPTION OF THE DRAWINGS

FIG. 6 is one embodiment of the separation means comprising a tear-drop shaped structure mounted on the exterior surface of the distal end of the catheter, wherein the self condensing pH sensor is recessed within said distal end of said catheter and a light emitting diode (LED) is mounted in the tip for illumination.

FIG. 7 is another embodiment of the separation means comprising an inflatable/deflatable balloon located near the distal end of the catheter.

FIG. 8 is another embodiment of the separation means comprising a plurality of flexible trapezoid shaped structures extending from the exterior surface of the distal end of the catheter.

FIG. 9 is another embodiment of the separation means comprising a plurality of wire structures extending from the exterior surface of the distal end of the catheter.

FIG. 10 is another embodiment of the separation means comprising a plurality of ring structures coaxially engaged to the exterior surface of the distal end of the catheter.

FIG. 11 is a graphic representation of the monitoring means demonstrating the expected wave format for a non-hydrated, partially hydrated and fully hydrated pH sensor.

FIG. 12 is a schematic representation of the electrical circuit used in the transmitting device for monitoring the hydration level of the pH sensor.

DESCRIPTION OF THE PREFERRED EMBODIMENTS

Figure 1:
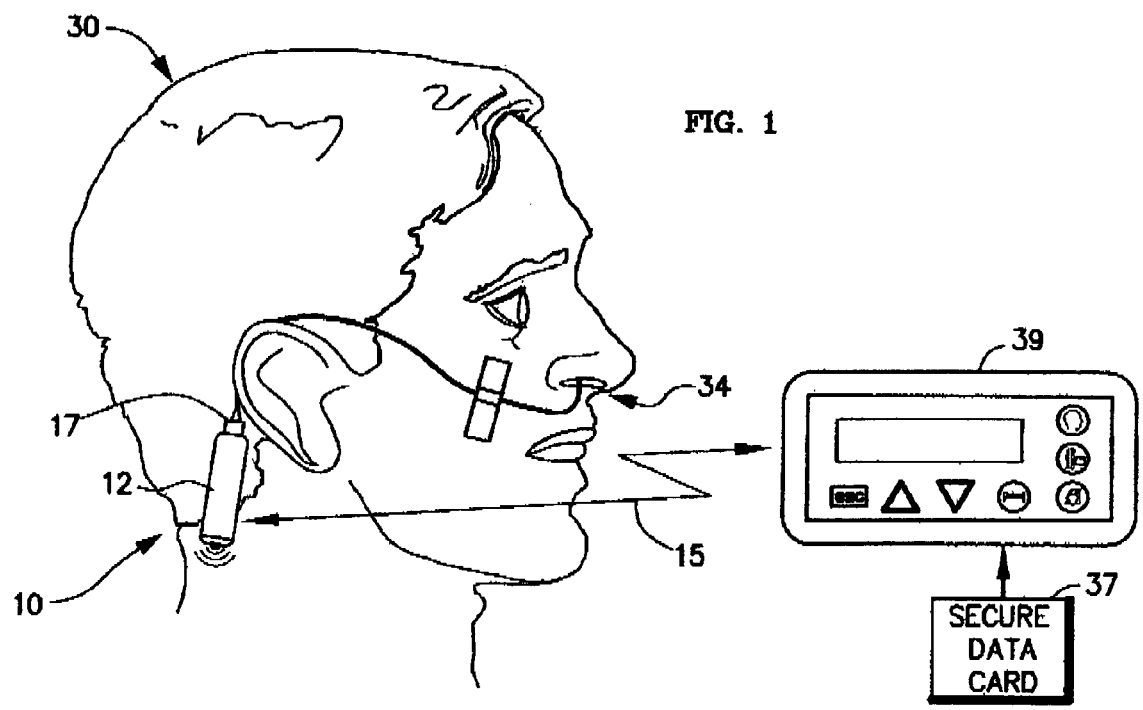
FIG. 1 is a perspective representation of the present invention system, showing the proximal end of the catheter exiting one nostril and draped over the ear of a typical patient, and a wireless transmitting device which communicates with a processing receiver/data recorder.

The present invention is a system comprising a plurality of components, including a self-condensing pH sensor distally mounted on a catheter, a transmitter with hydration sensing circuitry for the pH sensor, and processing receiver/data recorder. Referring to FIG. 1, a perspective representation of the present invention system 10 is shown where the catheter 18 is exiting one nostril 34 and draped over the ear of a typical patient 30. The proximal end 17 of the catheter 18 is connected to a transmitting device 12, which communicates with a processing receiver with data recording capability 39 (herein referred to the "processing receiver/data recorder" 39). The preferred method of communication is by wireless means 15, however, it is anticipated by the Applicants that the transmitting device can communicate with the processing receiver/data recorder 39 by a direct wired means. The wireless transmitter device 12 incorporates an antenna that transfers the measured pH data by employing one of many wireless methods, such as radio-frequency (RF) energy. Other methods of wireless transmitting include optical and infrared means and Bluetooth™ technology.

The processing receiver/data recorder 39 is designed as the operator interface between both the clinician and patient, and a means for recording pH data and user events during an ambulatory study. The processing receiver/data recorder 39 is typically battery powered, include a clock to keep and display time, memory to store patient data, buttons for recording patient events, and a connection to a pH sensor/amplifier front end. This connection can be wired or wireless. Additionally, the recorder typically provides a way to upload the data to a PC for storage and analysis. The processing receiver/data recorder 39 includes low power microprocessors such as Microchip model 16F and 18F series controllers, and the ATMEL 8051 family of devices. Timekeeping operations are accomplished by the microprocessor, or alternately accomplished by a dedicated time chip such as the Dallas DS1338 real time clock. To keep power consumption to a minimum, LCD displays such as the Optrex DMC-16204 is utilized. Wireless communication can be accomplished in a variety of means, from very simple frequency shift keying techniques to technically advanced spread spectrum designs.

Before an ambulatory pH study is started, the clinician typically calibrates the pH sensor with calibration buffer solutions of know values. The processing receiver/data recorder 39 prompts the user on what to do, interprets the digital signal output from the sensor/transmitter while in the various buffer solutions, calculates calibration factors and stores them in non-volatile memory. Other parameters such as time/date adjustment, study duration, and display options can also be adjusted at this time.

After successful calibration is completed and the clinician has setup the unit to their satisfaction, the processing receiver/data recorder 39 is given to the patient 30 and instructed on its use. The front of the processing receiver/data recorder 39 has a multitude of buttons that are pressed by the patient 30 to record symptoms and activities. Symptoms such as heartburn, and coughing are recorded at the time the patient feels the onset of these events and will be compared to the pH values recorded during these time periods. Activities such as meals, supine (laying down) are also logged and used by the physician to assist in making a proper diagnosis.

The processing receiver/data recorder 39 includes a removable data card 37 that stores the measured pH data for subsequent analysis. Recording data card 37 can one of the typical marketed non-volatile memory devices such as the Secure Digital™ (SD), Multimedia Card™ (MMC), Compact Flash™, mart Media™, or can be a proprietary developed data card. Other types of non-volatile media that can be used as recording capability are CD-ROMs, DVDs, and hard disks. Once a removable data card 37 with stored data is removed, a new removable data card can be inserted for recording the next patient study of pH data. The processing receiver/data recorder 39 can also include outputs to other data recording devices, such as equipment used in hospitals and sleep clinics.

The processing receiver/data recorder 39 also includes software that is specifically designed to analyze waveforms generated by the waveform input hydration sensing circuitry located in the transmitter 12. The software is programmed to initiate a visual or audible alarm and/or stop recording pH data upon the occurrence of unreliable waveforms. The processing receiver/data recorder 39 can also incorporate an alerting means that is initiated when certain pH parameters are measured. For example, if the pH enters a range known to be associated with a particular respiratory disease, a visual or audible alarm can be generated.

Figure 2:
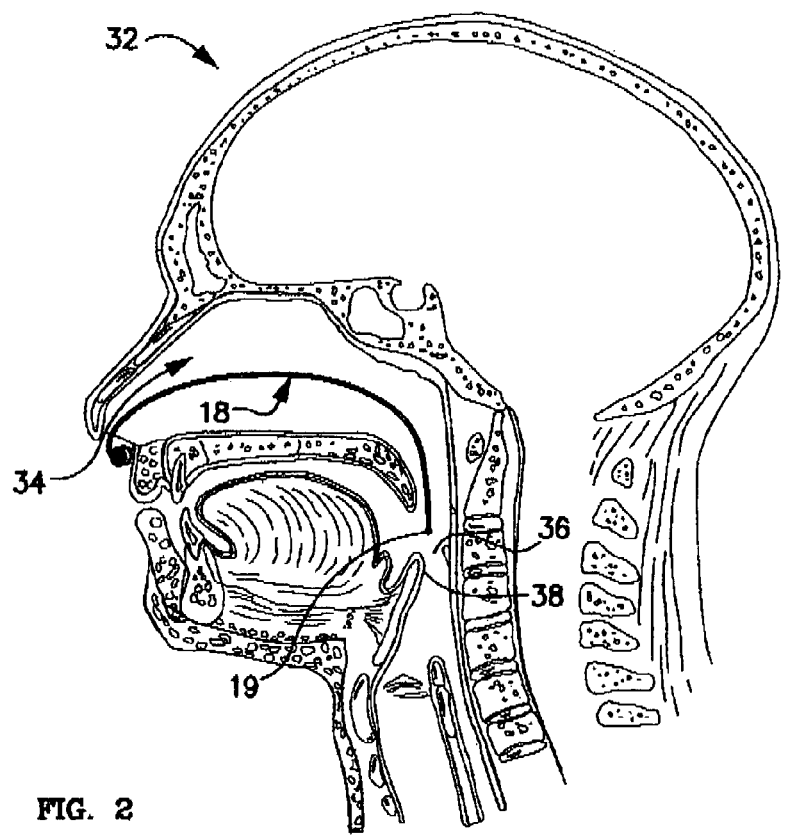
FIG. 2 is cross-sectional representation of the present invention system, showing the location of the distal end of the catheter comprising a self condensing pH sensor positioned above the epiglottis.

FIG. 2 is a cross-sectional representation of a typical patient 32 with the present invention system 10, properly inserted through the nasal passages 34. The distal end of the catheter 19 containing a self condensing pH sensor 20 is positioned above the epiglottis 38. The positioning of the pH sensor 20 is important for monitoring real-time pH while providing comfort for the patient and not interfering with other patient functions such as swallowing and talking. Methods for verifying the position of the distal end of the catheter in the patient's oropharynx region 36 include calibrated markings on the catheter shaft. The sensor position can also be visually established. To simplify placement, another embodiment includes in the distal end 19 of the catheter 18 an embedded light source, such as a light emitting diode (LED), which can be illuminated continuously or in a flashing mode to aid in positioning the distal pH sensor 20 in the oropharynx region 36 of a cross-sectional 32 patient 30.

Figure 3:
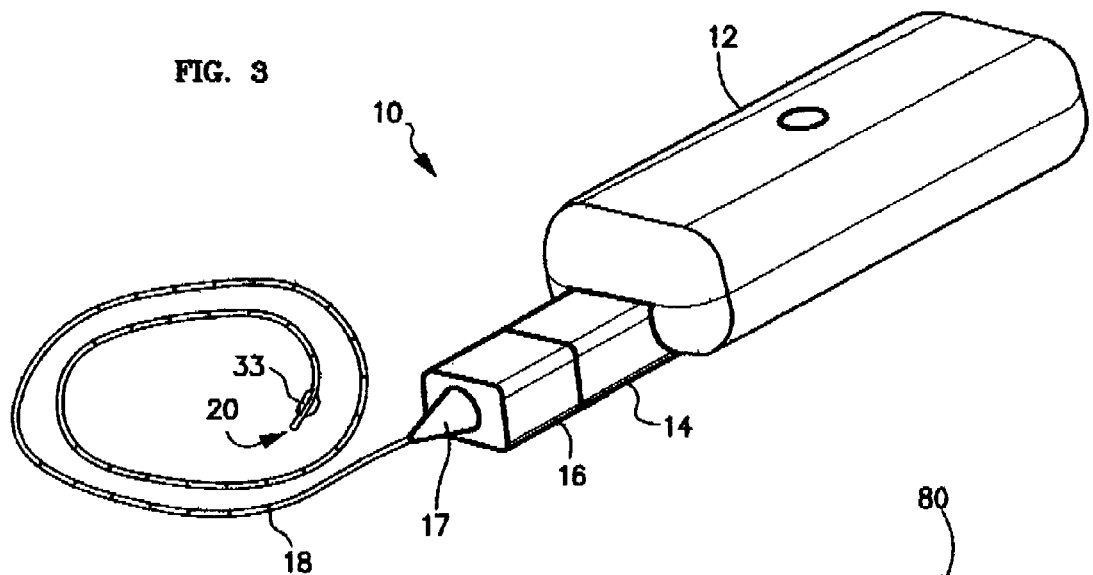
FIG. 3 is a representation of the entire catheter length with a self condensing pH sensor and separation means located on the distal end of the catheter and a transmitting device located on the proximal end of the catheter.

FIG. 3 is a representation of the entire catheter length with a self condensing pH sensor 20 and separation means 33 located on the distal end of the catheter 19 and a transmitting device 12 located on the proximal end 17 of the catheter 18. A connector 16 on the catheter is shown engaged to a receiving connector 14 on the transmitting device 12. The catheter 18 can be a single or a multi-luminal design for allowing electrical connection from the distal pH sensor to extend throughout the longitudinal length of the catheter and terminate in the transmitter 12, located on the proximal end 17 of catheter 18. In addition, in the embodiment (shown in FIG. 7) where an inflatable balloon 44 is used as a separation means, an inflation/deflation lumen can be incorporated into the catheter design to allow communication from the inflation balloon along the longitudinal length of the catheter and terminating at a proximally located transmitter body. The outer tubular member of the catheter 18 generally has an outside diameter in the range of 0.030" to 0.090", and preferably between 0.050" and 0.070". Its wall thickness is typical for its diameter and generally is in the range of 0.005" to 0.020" and preferably between 0.010" and 0.015". The materials used to fabricate the catheter are typical thermoplastic polymers such as polyethylene, polyether block amide, polypropylene, polyvinyl chloride (PVC), polystyrene, ABS, nylon, delrin, polyethylene terephthalate (PET), polytetrafluoroethylene (PTFE), polyurethane composites, and elastomeric materials.

The transmitter 12 located on the proximal end 17 of the catheter 18 contains an electrical circuit to communicate, preferably wirelessly 15 (as shown in FIG. 1), pH information to a processing receiver/data recorder 39. The transmitter 12 comprises a circuit board populated with various discrete and semiconductor components and mounted in a housing. The housing is generally fabricated from a polymeric material such as, polycarbonate, acrylic, polysulfone, polyethylene, polypropylene, polystyrene, ABS, nylon, delrin, or polyurethane composites. A connector 14 is designed to engage with a connector 16 located on the proximal end 17 of the catheter 18. A means can be incorporated into the housing which allows the housing to be recoverably secured to the patient or simply draped over a patient's ear as shown in FIG. 1. It is also anticipated by the Applicants that the transmitter 12 can be connected to the processing receiver/data recorder using typical hard wiring techniques.

In the wireless design, the transmitter 12 receives input from the pH sensor on a real time basis and sends this analog data, at a specified frequency, to a remotely located processing receiver/data recorder 39. The wireless transmitter device 12 incorporates an antenna that transfers the pH data using wireless methods, such as radio-frequency (RF), optical and infrared means. The antenna can extend externally from the transmitter housing or can be concealed inside the housing.

The transmitter 12 also contains circuitry 70 to interrogate the hydration level of the pH sensor. The hydration monitoring circuitry 70 is shown in more detail in FIG. 12.

Figure 4:
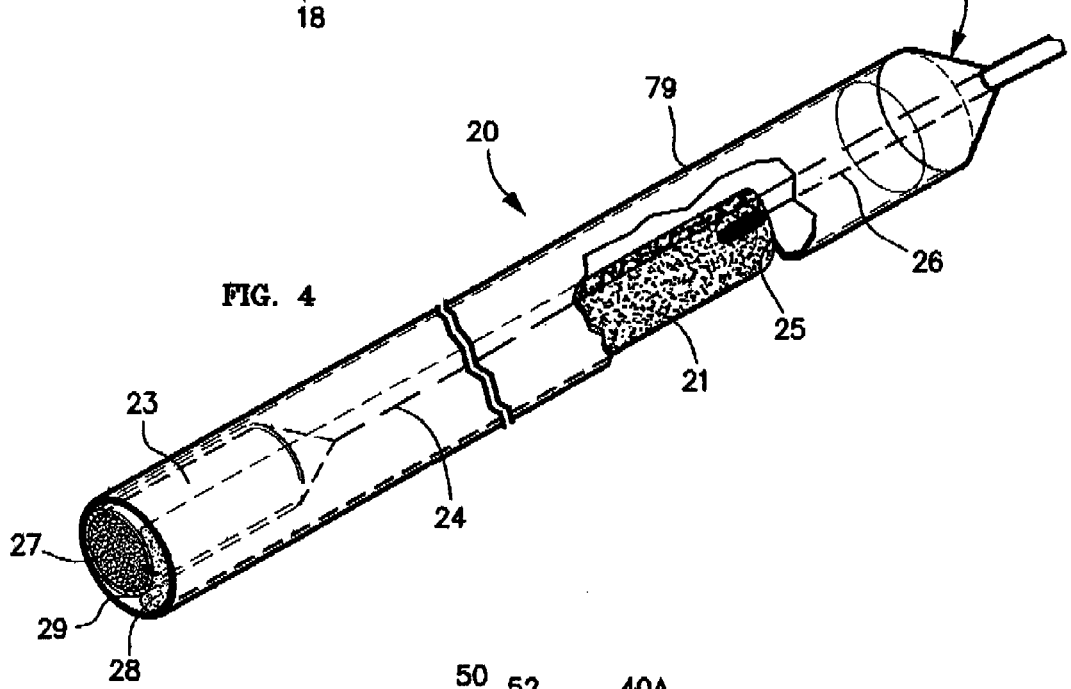
FIG. 4 is a partially sectional side view of the self condensing pH sensor demonstrating, in detail, the orientation and components of the pH sensing means, including the position of the reference wick surrounding an inner collinearly positioned tubular member containing the antimony sensor.

FIG. 4 is a partially sectional side view of the self condensing pH sensor 20 demonstrating in detail the orientation and components of the pH sensing means 20, including the position of the reference wick 28 surrounding an inner co-linearly positioned tubular member containing the antimony element 23.

The self-condensing pH sensor 20 is located within the tubular member of catheter 18 and is either co-linearly or coaxially aligned within the outer tubular member. The pH sensor also includes an inner tubular member 29 that is usually fabricated by an extrusion or dip coating process using a variety of polymeric materials including polyimide, polyethylene, polypropylene, polyvinyl chloride, polyether block amide, polystyrene, ABS, nylon, delrin, polyethylene terephthalate (PET), fluorinated ethylene-propylene (FEP) or polytetrafluoro-ethylene (PTFE). The inner tubular member 29 has an outside diameter smaller than the inside diameter of the outer catheter and generally is in the range of 0.015" to 0.030", and preferably between 0.020" and 0.028". Its wall thickness is typical for its diameter and generally is in the range of 0.00025" to 0.002" and preferably between 0.0005" and 0.001".

Located within the inner tubular member 29 is an antimony element 23 having a surface area at the terminal end 27. The antimony element 23 is generally 99% pure and free from significant contaminants. The Applicant contends that the antimony element 23 could be replaced with other metallic substances similar to antimony which exhibit a change in electrical potential when immersed in different pH fluids. Furthermore, other potential sensor elements such as specially formulated polymers, semiconductor technology, Ion Sensitive Field Effect Transistors ("ISFET's), optical sensing, capacitive sensing, and nanotechnology could be employed.

The antimony element 23 is engaged at its proximal end to an electronic communication means 24. Typically the electronic communication means comprises electrical wire that has an internal core comprising an electrically conductive metallic material, which is encased by a nonconductive jacket. The means of engagement typically employs standard soldering technology and can be supported by a variety of means to provide strain relief. The terminal surface 27 of the antimony element 23 defines the distal terminal boundary of the sensor 20 and is the surface that is exposed to liquid or humid gaseous environments. As shown in FIG. 4, the antimony element 23 and the reference wick 28 are substantially in the same plane. However, it is anticipated by the Applicants that several designs or embodiments in which the antimony element and reference electrode are not substantially in the same plane. For example, a coaxial design in which the antimony element, protruding beyond the center of the sensor terminal end, has the advantage of providing a greater surface area of antimony element to react with the condensing sample. In addition, a co-linear sensor in which the antimony sensor protrudes past the plane of the wick and the extension that is angled towards the wick provides the advantage of providing a greater surface area but additionally diminishes or reduces the contact angle between the antimony element and reference wick. Reducing the angle between the wick and the antimony element may provide a more reliable measurement in low humidity conditions. Still another design or embodiment entails either the coaxial or co-linear design, where the antimony element is recessed from the plane of the wick. This design has the potential for greater stability due to the larger film thickness that condenses and resides on the antimony face. In addition, a further benefit of this design is the potential for greater sensitivity in sleep apnea clinical conditions due to the increased angle between the electrodes at the top of the recess. This increased angle may cause the surface tension to break contact between the electrodes more rapidly than on a planar design in the event of a decrease in fluid deposition.

The performance of the sensor 20 may be enhanced in some environments by the inclusion of a coating (not shown) on this distal surface. One example would be a hygroscopic coating to enhance the absorption and retention of moisture on the sensor in humidified gases and aerosols. Materials such as hydrophilic polyurethanes, polyacrylamides, poly(2-hydrox-ethyl-methacrylate), other methacrylate copolymers, perfluorinated polymers, polysaccharides, polyvinylchloride polyvinyl alcohol and silicones could all be utilized as surface enhancements either alone, in combination, or with modifications.

The use of a hygroscopic coating may also enable the use of other sensor configurations by enhancing the ability of the reference and pH elements to remain in contact through periods of little or no fluid contact. One example is a side mounted reference sensor in close proximity to a pH sensing element located on the sensor end. A second design which would benefit from a coating in this application includes reference and sensing elements placed on the sides of the catheter tube either opposed or linearly. The coating may also provide benefits by maintaining continuity between multiple sensors and a single reference.

Located proximally, from a range of 1-10 millimeters from the proximal end of the antimony element 23 and preferably 4-5 millimeters is a reference element 25. Said reference element 25 is primarily composed of a silver core surrounded with a coating of silver chloride. A technology of dipping a silver core in a high temperature bath of silver chloride to produce the silver chloride coating is employed in the present invention. Other means of producing the silver chloride coating exist, including electro-deposition and vapor deposition. The resulting coating generally is 0.0001" to 0.010" in thickness, and preferably 0.001" to 0.005". The reference element 25 is engaged to an electrical communication means 26, e.g. typical wire that extends to the proximal end 17 of the outer tubular member or catheter 18 and can terminate in a typical electrical connector 16. An adhesive or polymer plug can be placed in a proximal position to the reference element 25 that is engaged to the outer tubular member or catheter 18 which provides support for electrical communication means 24,26 and provides proximal sealing of the outer tubular member or catheter 18.

A reference wick 28 is located between the inside surface of the outer tubular member of the self-condensing pH sensor 20 and the outer surface of the inner tubular member 29. In one embodiment the inner tubular member 29 is coaxially offset with the outer tubular member. The reference wick 28 partially surrounds the inner tubular member 29 where the area of the offset coaxial design is large enough to contain the fabric or mesh configuration of the reference wick 28. As discussed in more detail below, the reference wick 28 has a mesh or fibrous configuration which functions to entrain or retain an ion conducting fluid 21.

Reference wick 28 is physically separated from the antimony element 23 by the wall of the inner tubular member 29. It is important to the present invention that the reference wick 28 does not engage or contact the antimony element 23 at any point. The reference wick 28 can be fabricated from a variety of polymeric based materials. Examples of such materials are polysaccharides, polyester, polyethylene, polypropylene, polyvinyl chloride (PVC), polystyrene, ABS, nylon, delrin, polyethylene terephthalate (PET), polytetrafluoroethylene (PTFE), collagen, Hytrel (thermoplastic polyester elastomer), or any material or combination of materials which exhibit a weave, felt or mesh design that facilitates wicking or ion conduction. One example of a preferable material for the reference wick 28 is a polyester fabric mesh. The reference wick 28 functions similarly to a plurality of capillary tubes which facilitate the transport of ions between the antimony element 27 and reference element 25.

The reference wick 28 is impregnated with an ion conduction fluid 21. Typical conduction fluids include those that contain sodium chloride or potassium chloride and water. One example that can be used with the sensor is a saturated aqueous solution of sodium chloride containing from 1-10 percent polysaccharide, with a preferred range of 1-3 percent. Other materials that can function as the reference wick 28 with an ion conduction fluid 21 include ion carrying gels, hydrogels, open cell foams and porous frits of various materials. These gels, hydrogels, and other materials aid in reducing the diffusion of contaminants into the ion conduction fluid.

Due to the design, position on the distal end 19 of the catheter 18, the size of the components, and location in the patient's airway, the pH sensor 20 of the present invention is self condensing. In the moist environment of the oropharynx region 36, droplets condense on the terminal surface 27 and create an electrical connection between reference wick 28 and the antimony element 23 allowing the sensor to operate in measuring the pH of the condensed droplets.

Figure 5:
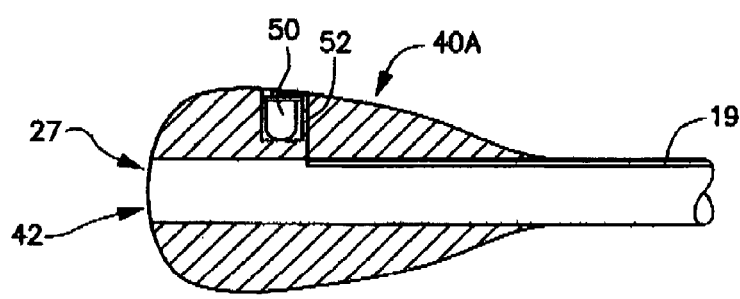
FIG. 5 is one embodiment of the separation means comprising a sectional view of a tear-drop shaped structure mounted on the exterior surface of the distal end of the catheter, wherein the self condensing pH sensor is mounted flush with said distal end of said catheter and a light emitting diode (LED) is mounted in the tip for illumination.

FIG. 5 is one embodiment of the present invention with separation means 40a comprising a cross section of the tear-drop shaped structure 43 mounted on the exterior surface of the distal end 19 of the catheter 18. The tear-drop shaped structure 43 is designed to provide separation means when the catheter 18 and distally mounted pH sensor 20 are positioned above the epiglottis 38. In this embodiment, the self condensing pH sensor 20 is mounted flush 42 with said distal end 27 of the catheter 18. The tear-drop shaped structure 43 is adhered to the outside surface of the catheter 18 using general adhesive technology. The distal end of the tear-drop shaped structure 43 generally has an outside diameter in the range of 0.040" to 0.250", and preferably between 0.100" and 0.150". The outside diameter then slopes towards the proximal end of the tear-drop shaped structure 43 where it approximates the outside diameter of the catheter 18. The tear-drop shaped structure 43 is usually fabricated by machining or molding means using a variety of polymeric materials including polyimide, polyethylene, polypropylene, polyvinyl chloride, epoxy, polyurethane, polycarbonate, acrylic, polystyrene, ABS, nylon, delrin, polyethylene terephthalate (PET), polyether block amide, fluorinated ethylene-propylene (FEP) or polytetrafluoro-ethylene (PTFE). As shown in this FIG. 5, to simplify placement within the oropharynx region of a patient, an embedded light source 50 is included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36. The light source 50 functions to illuminate the distal end of the catheter and the anatomical features of the patient's airway for observation by the clinician, thereby facilitating proper placement of the measurement device.

FIG. 6 is another embodiment of the present invention with separation means 40a comprising a cross section of the teardrop shaped structure 43 mounted on the exterior surface of the distal end 19 of the catheter 18. The tear-drop shaped structure 43 is designed to provide separation means when the catheter 18 and distally mounted pH sensor 20 are positioned above the epiglottis 38. In this embodiment, the self condensing pH sensor 20 is recessed 41 in the range of 0.005" to 0.020", and preferably 0.010" to 0.015" within said distal end of said catheter. The tear-drop shaped structure 43 is adhered to the outside surface of the catheter 18 using general adhesive technology. The distal end of the tear-drop shaped structure 43 generally has an outside diameter in the range of 0.040" to 0.0250", and preferably between 0.100" and 0.150". The outside diameter then slopes towards the proximal end of the tear-drop shaped structure 43 where it approximates the outside diameter of the catheter 18. A tear-drop shaped structure 43 is usually fabricated by a machining or molding process using a variety of polymeric materials including polyimide, polyethylene, polypropylene, polyvinyl chloride, epoxy, polyurethane, polycarbonate, acrylic, polystyrene, ABS, nylon, delrin, polyethylene terephthalate (PET), polyether block amide, fluorinated ethylene-propylene (FEP) or polytetrafluoro-ethylene (PTFE). As shown in this FIG. 6, to simplify placement within the oropharynx region of a patient, an embedded light source 50 is included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36. The light source 50 functions to illuminate the distal end of the catheter and the anatomical features of the patient's airway for observation by the clinician, thereby facilitating proper placement of the measurement device.

FIG. 7 is another embodiment of the present invention with separation means 40b comprising an inflatable/deflatable balloon 44 located near the distal end 19 of the catheter 18. In this embodiment, an inflation and deflation lumen (not shown) can be incorporated into the catheter shaft design. The inflation and deflation lumen would communicate with a port inside of the balloon 44 and attach to a sealed connector 46 on the proximal end 17 of the catheter 18. The balloon 44 is design to be in a deflated and contracted orientation when clinically inserting and withdrawing the catheter through the nasal passages 34 of the patient 30. When the catheter 18 and the self condensing pH sensor 20 are positioned above the epiglottis 38, the balloon is inflated to provide the separation means 40b from the tissues of the oropharynx region 36. Although not shown in FIG. 7, to simplify placement within the oropharynx region of a patient, an embedded light source 50 can be included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36.

FIG. 8 is another embodiment of the present invention with separation means 40c comprising a plurality of flexible trapezoid shaped structures 45 extending from the exterior surface of the distal end of the catheter. The outer edge of the flexible trapezoid shape structures 45 projects outward from the catheter in the range of 0.010" to 0.100", preferably between 0.025" and 0.050". The flexible trapezoid shaped structures 45 are designed to provide separation means when the catheter and distally mounted pH sensor are positioned above the epiglottis. The flexible trapezoid structures 45 are usually fabricated using a standard cutting or molding process and adhere to the outside surface of the catheter 18 using general adhesive technology. The number of flexible trapezoid structures can vary from 2 to 8, but preferably 3 mounted at approximately 120 degrees apart or 4 mounted at approximately 90 degrees apart. A variety of polymeric materials can be used including polyimide, polyethylene, polypropylene, polyvinyl chloride, polyurethane, polycarbonate, acrylic, polystyrene, ABS, nylon, delrin, polyethylene terephthalate (PET), fluorinated ethylene-propylene (FEP) or polytetrafluoro-ethylene (PTFE). Although not shown in FIG. 8, to simplify placement within the oropharynx region of a patient, an embedded light source 50 can be included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36.

FIG. 9 is another embodiment of the present invention with separation means 40d comprising a plurality of wire structures 46 extending from the exterior surface of the distal end 19 of the catheter 18. The outer edge of the wire structures 46 projects outward from the catheter in the range of 0.010" to 0.100", preferably between 0.025" and 0.050". The diameter of the wire structures is in the range of 0.010" to 0.020", preferably 0.012" to 0.014". The wire structures 46 are designed to provide separation means when the catheter and distally mounted pH sensor are positioned just above the epiglottis. The wire structures 46 are usually fabricated using a standard cutting and bending process and adhered to the outside surface of the catheter using general adhesive technology. The number of wire structures 46 can vary from 2 to 8, but preferably 3 mounted at approximately 120 degrees apart or 4 mounted at approximately 90 degrees apart are used. A variety of metallic materials including stainless steel, spring steels, gold alloys, and other alloys can be used to fabricate the wire structures. Although not shown in FIG. 9, to simplify placement within the oropharynx region of a patient, an embedded light source 50 can be included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36.

FIG. 10 is another embodiment of the present invention with separation means 40e comprising a plurality of ring structures 48 coaxially engaged to the exterior surface of the distal end 19 of the catheter 18. The outer edge of the plurality of ring structures 48 projects outward from the catheter in the range of 0.010" to 0.050", preferably between 0.020" and 0.030". The plurality of ring structures 48 are designed to provide separation means when the catheter and distally mounted pH sensor are positioned above the epiglottis. The plurality of rings 48 are usually fabricated using a standard cutting or molding process and adhered to the outside surface of the catheter using general adhesive technology. The number of plurality of ring structures 48 can vary from 2 to 8, but preferably 3 mounted or 4 mounted are used. A variety of polymeric materials including polyimide, polyethylene, polypropylene, polyvinyl chloride, elastomers, polyurethane, polycarbonate, acrylic, polystyrene, ABS, nylon, delrin, polyethylene terephthalate (PET), fluorinated ethylene-propylene (FEP) or polytetrafluoro-ethylene (PTFE). Although not shown in FIG. 10, to simplify placement within the oropharynx region of a patient, an embedded light source 50 can be included in close proximity to the distal end 19 of the catheter 18. The light source 50 is connected to an electrical wiring means 52 that extends the length of the catheter, incorporated as an element of the connectors 14, 16 and is connected to a power source in the transmitter 12. The embedded light source 50 preferably is comprised of a light emitting diode (LED), which can be illuminated continuously or in a flashing mode to aid in determining the location of the distal pH sensor 20 in the oropharynx region 36.

FIG. 11 is a graphic representation of the hydration sensing means 60 demonstrating the expected wave format for a non-hydrated 65, partially hydrated 66 and fully hydrated 67 states of the pH sensor. The waveform 65 demonstrates that the self-condensing pH Sensor is not hydrated. The waveform 66 demonstrates that the self-condensing pH Sensor is partially hydrated. The waveform 67 demonstrates that the self-condensing pH Sensor is fully hydrated. If the sensor loses hydration or malfunctions, data generated may be unreliable. The hydration sensing circuitry 70 detects these conditions by sending a small electrical waveform (approximately 0.5V Peak to Peak waveform) to the sensor and then looks at the composite signal information generated back from the sensor. This information is sent to the processing receiver/data recorder 39 which analyzes the data. If the analysis of the data shows a relatively stable reading from peak to peak, the pH data is accepted and recorded. If the data shows relatively high peak to peak reading, the pH data is not recorded and then the apparatus signals that the data may be unreliable.

FIG. 12 is a schematic representation of the hydration sensing circuit 70 used in the transmitting device 12 for sensing the hydration level of the pH sensor 20. The hydration monitor circuit 70 periodically sends a low voltage signal through input circuitry 77 and electronic communication means 74, 75 to the pH sensor 20. After the low voltage signal is sent to the pH sensor 20, output circuitry 78 analyzes the resulting wave forms as discussed above in FIG. 11.

By way of example, in clinical operation of the present invention, the physician generally applies a medicament to anesthetize a patient's nasal passages before inserting the self-condensing pH sensor and catheter apparatus 10. The clinician will then position the sensor 20 located at the distal end 19 of the catheter 18 so that is positioned in the oropharynx region above the epiglottis. In this position, the patient does not feel discomfort during normal activities such as talking, eating, or drinking. The proximal end 17 of the catheter 18 is then secured to their face with tape or other means to ensure that it stays in the appropriate position.

During the pH measurement study, the patient can wear the processor receiver/data recorder 39 with a provided carrying case or alternately it can be place in a convenient location within the room where the patient resides. The transmitter 12 can be releasably attached to the patient with tape or other appropriate means. The patient continues to wear the inserted catheter 18 with self-condensing sensor 20 for the duration of the study.

The patient is instructed to press the corresponding button on the processing receiver/data recorder when any of the following events occur during the study period:
 a. Cough (press at the onset of the symptom; if it lasts for a long time, they press the button again after the symptom has stopped)
 b. Eat a meal or snack; drink a beverage (press button when they begin and when they finish eating or drinking).
 c. Lie down in a supine position (when they lie down and again when they get up).
 d. Experience chest pain or heartburn (press at the onset of the symptom; if it lasts for a long time, they press the button again after the symptom has stopped).

We claim:

1. An apparatus for monitoring pH, said apparatus comprising:
 a catheter apparatus having a distal end, a proximal end, and at least one lumen that extends along the longitudinal length of said catheter apparatus and communicating with said distal end and said proximal end;
 a self-condensing pH sensor located in close proximity to said distal end, said self-condensing pH sensor designed to be positioned in the upper airway of a patient;
 a data transmitter attached to said catheter proximal end;
 said self-condensing sensor in electrical communication with said data transmitter; and
 a processing receiver/data recorder in communication with said data transmitter.

2. The apparatus for monitoring of pH as recited in claim 1, wherein said catheter has separation means to restrain said self-condensing sensor element from directly contacting the airway mucosal membranes of a patient, said separation means located near said distal end of said catheter.

3. The apparatus for monitoring of pH as recited in claim 2, wherein said separation means comprises a tear-drop shaped structure.

4. The apparatus for monitoring of pH as recited in claim 3, wherein said tear-drop shaped structure is fabricated from an elastomeric, polymeric or urethane material.

5. The apparatus for monitoring of pH as recited in claim 2, wherein said separation means is an expandable balloon.

6. The apparatus for monitoring of pH as recited in claim 2, wherein said separation means comprises one or more trapezoidal shaped structures.

7. The apparatus for monitoring of pH as recited in claim 6, wherein said trapezoidal shaped structures are fabricated from an elastomeric, polymeric or urethane material.

8. The apparatus for monitoring of pH as recited in claim 2, wherein said separation means comprises a plurality of wires extending from said distal end of said catheter.

9. The apparatus for monitoring of pH as recited in claim 2, wherein said separation means comprises a plurality of ring structures coaxially engaged to an exterior surface of said distal end of said catheter.

10. The apparatus for monitoring of pH as recited in claim 9, wherein said ring structures are fabricated from an elastomeric, polymeric or urethane material.

11. The apparatus for monitoring of pH as recited in claim 1, wherein said processing receiver/data recorder is in wireless communication with said data transmitter.

12. The apparatus for monitoring of pH as recited in claim 11, wherein said wireless communication is conducted in real-time.

13. The apparatus for monitoring of pH as recited in claim 1, wherein said processing receiver/data recorder is in wired communication with said data transmitter.

14. The apparatus for monitoring of pH as recited in claim 1, wherein said processing receiver/data recorder has the capability to analyze the hydration level of said self condensing pH sensor.

15. The apparatus for monitoring of pH as recited in claim 1, further comprising a light source mounted on said catheter in close proximity to said distal end.

16. The apparatus for monitoring of pH as recited in claim 15, wherein said light source is a light emitting diode.

17. The apparatus or monitoring of pH as recited in claim 1, further comprising a removable data storage medium, said removable data storage medium designed to communicate with said processing receiver/data recorder, said removable data storage medium further designed to store recorded pH measurements monitored by said self-condensing pH sensor over a period of time.

18. The apparatus for monitoring of pH as recited in claim 1, wherein said processing receiver/data recorder includes a visual or auditory alarming means that is generated upon the occurrence of a certain pH range.

19. An apparatus for monitoring of pH as recited in claim 1, further comprising a coating on a portion of said self-condensing sensor, said coating including hydrophilic polyurethanes, polyacrylamides, poly (2-hydrox-ethyl-methacrylate) other methacrylate copolymers, perfluorinated polymers, polysaccharides, polyvinylchloride polyvinyl alcohol, silicones and any combinations thereof.

20. Apparatus for monitoring pH as recited in claim 1 further comprising an illuminating means for assisting the positioning of the self-condensing pH sensor in the oropharynx region.

21. An apparatus for monitoring of pH, said apparatus comprising:
a catheter apparatus having a distal end, a proximal end, and at least one lumen that extends along the longitudinal length of said catheter apparatus and communicating with said distal end and said proximal end;
a self-condensing pH sensor located in close proximity to said distal end, said self-condensing pH sensor designed to be positioned in the oropharynx area of a patient;
a data transmitter connected to said proximal end;
said self-condensing sensor in electrical communication with said data transmitter;
a processing receiver/data recorder in communication with said data transmitter; and
a separation means to restrain said self-condensing sensor from contacting the oropharynx membranes of a patient, said separation means located near said distal end of said catheter.

22. The apparatus for monitoring of pH as recited in claim 21, wherein said separation means comprises a tear-drop shaped structure.

23. The apparatus for monitoring of pH as recited in claim 22 wherein said tear-drop shaped structure is fabricated from an elastomeric, polymeric or urethane material.

24. The apparatus for monitoring of pH as recited in claim 21, wherein said separation means is an expandable balloon.

25. The apparatus for monitoring of pH as recited in claim 21, wherein said separation means comprises one or more trapezoidal shaped structures.

26. The apparatus for monitoring of pH as recited in claim 25, wherein said trapezoidal shaped structures are fabricated from an elastomeric, polymeric or urethane material.

27. The apparatus for monitoring of pH as recited in claim 21, wherein said separation means comprises a plurality of wires extending from said distal end of said catheter.

28. The apparatus for monitoring of pH as recited in claim 21, wherein said separation means comprises a plurality of ring structures coaxially engaged to an exterior surface of said distal end of said catheter.

29. The apparatus for monitoring of pH as recited in claim 28, wherein said ring structures are fabricated from an elastomeric, polymeric or urethane material.

30. The apparatus for monitoring of pH as recited in claim 21, wherein said processing receiver/data recorded includes a visual or auditory alarming means that is generated upon the occurrence of a certain pH range.

31. The apparatus for monitoring of pH as recited in claim 21, wherein said processing receiver/data recorder is in wireless communication with said data transmitter.

32. The apparatus for monitoring of pH as recited in claim 31, wherein said wireless communication is conducted in real-time.

33. The apparatus for monitoring of pH as recited in claim 21, wherein said processing receive/data recorder is in real-time wired communication with said data transmitter.

34. The apparatus for monitoring of pH as recited in claim 21, wherein said processing receiver/data recorder has the capability to analyze the hydration level of said self-condensing sensor.

35. The apparatus for monitoring of pH as recited in claim 21, further comprising a light source mounted on said catheter in close proximity to said distal end.

36. The apparatus for monitoring of pH as recited in claim 35, wherein said light source is a light emitting diode.

37. The apparatus for monitoring of pH as recited in claim 35, wherein said light source functions to facilitate the catheter insertion, placement and location of said self-condensing pH sensor above the epiglottis within said oropharynx area of a patient, said light source comprising a continuous or flashing light emitting diode (LED) embedded in the distal end of the catheter for providing a visual sighting means for the physician.

38. The apparatus for monitoring of pH as recited in claim 21, further comprising a removable data storage medium, said removable data storage medium designed to communicate with said processing receiver/data recorder, said removable data storage medium further designed to store recorded pH measurements monitored by said self-condensing pH sensor over a period of time.

39. The apparatus for monitoring of pH as recited in claim 21, said self-condensing pH sensor capable of dehydrating and re-hydrating on a breath-by-breath basis.

40. The apparatus for monitoring of pH as recited in claim 21, further comprising a measurement system that can include a means to activate an auditory and/or visual alarm when predetermined pH values are detected.

41. The apparatus for monitoring of pH as recited in claim 21, wherein separation means functions to prevent the pH sensor from becoming entrapped in the airway mucosal wall.

42. An apparatus for monitoring of pH as recited in claim 21, further comprising a coating on a portion of said self-condensing sensor, said coating including hydrophilic polyurethanes, polyacrylamides, poly(2-hydrox-ethyl-methacrylate), other methacrylate copolymers, perfluorinated polymers, polysaccharides, polyvinylchloride polyvinyl alcohol, silicones and any combinations thereof.

43. Apparatus for monitoring pH as recited in claim 21 further comprising an illuminating means for assisting the positioning the self-condensing pH sensor in the oropharynx region.

44. An apparatus for monitoring pH, said apparatus comprising:
  a catheter, said catheter having a proximal end and a distal end;
  a self-condensing pH sensor, said self-condensing located in close proximity to said distal end of said catheter,
  a data transmitter, said data transmitter locates in close proximity to said proximal end of said catheter;
  said self-condensing pH sensor in electrical communication with said data transmitter;
  a processing receiver/data recorder in communication with said data transmitter; and
  said processing receiver/data recorder in communication with said data transmitter, further comprising the capability to record said self-condensing pH sensor dehydration events in real-time.

45. Apparatus for monitoring pH as recited in claim 44 further comprising an illuminating means for assisting positioning the self-condensing pH sensor in the oropharynx region.

46. A method for monitoring pH in the upper airway of a patient;
  inserting a catheter apparatus through the nasal channels of a patient and into an upper airway of a patient, said catheter apparatus comprising a catheter communicating with a self-condensing pH sensor located in close proximity to a distal end of said catheter, a data transmitter connected to a proximal end of said catheter, wherein said self-condensing sensor is in electrical communication with said data transmitter, a processing receiver/data recorder in communication with said data transmitter, and a separation means to restrain said self-condensing sensor from contacting membranes of said upper airway of a patient;
  locating said distally mounted self-condensing pH sensor within the upper airway of a patient; and
  monitoring the pH in the upper airway of the patient in real-time.

47. Apparatus for monitoring pH as recited in claim 46 further comprising an illuminating means for assisting positioning the self-condensing pH sensor in the oropharynx region.

* * * * *